United States Patent [19]

De Lafonteyne

[11] Patent Number: 5,364,779
[45] Date of Patent: Nov. 15, 1994

[54] PROCESS FOR TRANSFORMING CELLS

[75] Inventor: Jean De Lafonteyne, Oudenaarde,

[73] Assignee: Solvay (Societe Anonyme) and Clovis Matton, N.V., Avelgem/Kerkhove,

[21] Appl. No.: 643,145

[22] Filed: Jan. 18, 1991

Related U.S. Application Data

[63] Continuation of Ser. No. 209,292, Jun. 20, 1988, abandoned.

[30] Foreign Application Priority Data

Jun. 22, 1987 [NL] Netherlands .......................... 8701450

[51] Int. Cl.$^5$ ...................... C12N 15/00; C12N 15/71; C12N 15/72; C12N 15/73
[52] U.S. Cl. .................................. 435/172.3; 536/23.7; 536/24.1
[58] Field of Search ............... 435/172.1, 172.3, 320.1; 536/27, 23.1, 24.1, 23.7; 935/6, 52, 56; 435/252.3-252.35

[56] References Cited

U.S. PATENT DOCUMENTS 4,506,013 3/1985 Hershberger et al. ............ 435/172.3
4,650,761 3/1987 Hershberger et al. ............ 435/172.3

OTHER PUBLICATIONS

Reeck et al.; Cell 50: 667 (1987).
Smithies et al.; Nature 317: 230 (1985).
Yoneda et al.; Biochem. Biophys. Res. Comm. 91: 1556 (1979).
Smith et al.; Cell 24: 429 (1981).
Dawkins, *The Extended Phenotype*, 1982, Oxford University Press, Oxford, pp. 85, 86, and 287.

*Primary Examiner*—James Martinell
*Attorney, Agent, or Firm*—John P. White

[57] ABSTRACT

The invention relates to a process for transforming cells and to a recombinant DNA molecule for use therein. Said recombinant DNA molecule is a multifunctional linker comprising a DNA sequence which is homologous to a part of the receptor genome, an operator sequence and either a sequence which allows replication in a microorganism or a sequence which allows for integrative recombination in a vector. Preferably, said multifunctional linker also contains a gene whose expression can be detected in a microorganism, a gene whose expression can be detected in the receptor, a sequence which promotes recombination, and/or a hairpin structure at one or both ends. The transformation process uses donor DNA coupled to the multifunctional linker and allows for early success followed by further characterization of the donor DNA and its phenotypic impact.

13 Claims, 2 Drawing Sheets

FIGURE 1A
BamHI-RSG-RS-attB-p op lac-Chi-BglII
FIGURE 1B
BamHI-XbaI-BglII-Chi-RSG-RS-p op lac-oriM-MSG-BamHI
FIGURE 1C
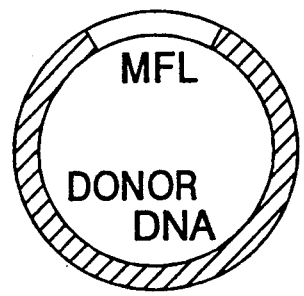
FIGURE 1D
MFL      DONOR DNA      MFL
FIGURE 1E
MFL      DONOR DNA + oriR      MFL

PROCESS FOR TRANSFORMING CELLS

This is a continuation of application Ser. No. 209,292, filed Jun. 20, 1988, now abandoned.

BACKGROUND OF THE INVENTION

This invention relates to a process for transforming cells and is in the field of recombinant DNA technology.

The hereditary properties of a cell can be artificially changed by means of recombinant DNA techniques by integrating foreign DNA into the DNA of this cell. This DNA may originate from other cells which need not have a connection with the organism to be transformed.

The object of this genetic manipulation is often to transmit genetic properties from cells having a specific desired hereditary property to cells not having this property. For instance, there is the transmission of resistance to a specific toxic product, e.g., a herbicide, from a resistant plant-species to a nonresistant variant of the same species or to a nonresistant other species within the same family or even to a nonresistant species of another, more or less related family. There is also the transmission of the ability of producing a substance useful for medicaments or other purposes, e.g., from plants producing that substance to plants growing in other climates and lacking the ability of producing the substance. Furthermore, there is the transformation of animal and even human cell lines so as to use them for the production of a desired substance. Genetic manipulation is often connected with great problems, e.g., owing to the dissimilarity of the structure and organization of the donor and receptor cell, and in particular the genome thereof.

In the methods hitherto described for transforming cells by means of recombinant DNA techniques the following procedure is generally adopted. A gene (or group of genes) coding for a specific desired property or a specific product is identified and isolated from a suitable donor cell. This gene is often obtained through copy DNA (cDNA) of the messenger RNA transcribed therefrom (mRNA). This DNA is then cloned in a vector which may be multiplied in a suitable microorganism. A great problem is often how to obtain a clone containing a complete copy of the desired gene. If this has proved to be a success, the gene is often to be provided with suitable regulatory elements for use in the receptor cell which may sometimes be strongly different from the regulatory elements of the donor cell. Finally, the gene including the regulatory elements is transmitted to the receptor cell by means of so-called shuttle vectors or by means of direct transformation methods.

These known processes for transforming cells have a number of drawbacks. In the first place, the isolation and characterization of the gene to be transmitted require a good deal of expensive research that has to be financed before one has a single transformant in hands. The nature of the research further involves that highly specialized laboratory facilities and highly qualified staff members are required such as they are available only in few places in the world.

Secondly, a very thorough examination of the regulatory elements and signals applicable in the receptor is required. Thirdly, it is necessary to construct vectors and shuttle vectors adapted to donor and receptor. For many receptor organisms suitable shuttle vectors have not yet been found or developed.

Consequently, there is a need for a process for transforming cells which does not show the above drawbacks.

SUMMARY OF THE INVENTION

The object of this invention is therefore to provide a simple, general, inexpensive and yet effective process for transforming cells. Cells are here to be taken to mean any kind of cells, such as cells of vegetable or animal (including human) origin, but also microorganisms, both prokaryotic microorganisms, such as bacteria, and eukaryotic microorganisms, such as fungi, yeasts, algae, etc.

This object can be achieved by means of the process according to this invention, which will be elucidated in the following paragraphs. This process comprises the use of a DNA molecule containing a number of special elements, the so-called multifunctional linker, which likewise forms part of the invention.

This invention further comprises a process for the preparation of the multifunctional linker and the parts thereof, which can be constructed beforehand in different combinations.

The process according to this invention comprises coupling of fragments of the donor genome to a multifunctional linker according to the invention and direct transformation to the receptor. The transformation occurs through recombination with a DNA sequence from the receptor, said sequence being incorporated into the multifunctional linker fort his purpose. Accordingly, after this step transformants are already available from which advantageous variants can be isolated, in principle, because of the properties transmitted. It is particularly advantageous that these variants can now be applied directly, with no detailed knowledge of the DNA sequences transmitted being required, or without having to isolate them. The exploitation of these transformants may yield the finances for further research.

A next phase comprises isolating the DNA of high molecular weight from the transformed receptor cells, fragmenting same and isolating the fragments containing the multifunctional linker and the donor DNA. These fragments are cloned in a microorganism to obtain a limited gene-bank. With these genes receptors are transformed so as to be able to correlate the DNA sequences with the phenotypic expression.

The process according to this invention and the multifunctional linker as well as its preparation will be discussed in more detail in the following paragraphs.

BRIEF DESCRIPTION OF THE FIGURES

FIG. 1A shows a multifunctional linker (MFL) suitable for integration in a phage lambda vector.

FIG. 1B shows a multifunctional linker suitable for multiplication and selection in a microorganism without a vector.

FIG. 1C shows circularized donor DNA.

FIG. 1D shows linear donor DNA with hairpin ends.

FIG. 1E shows linear donor DNA with replication functions of the receptor and hairpin ends.

Figure 2:
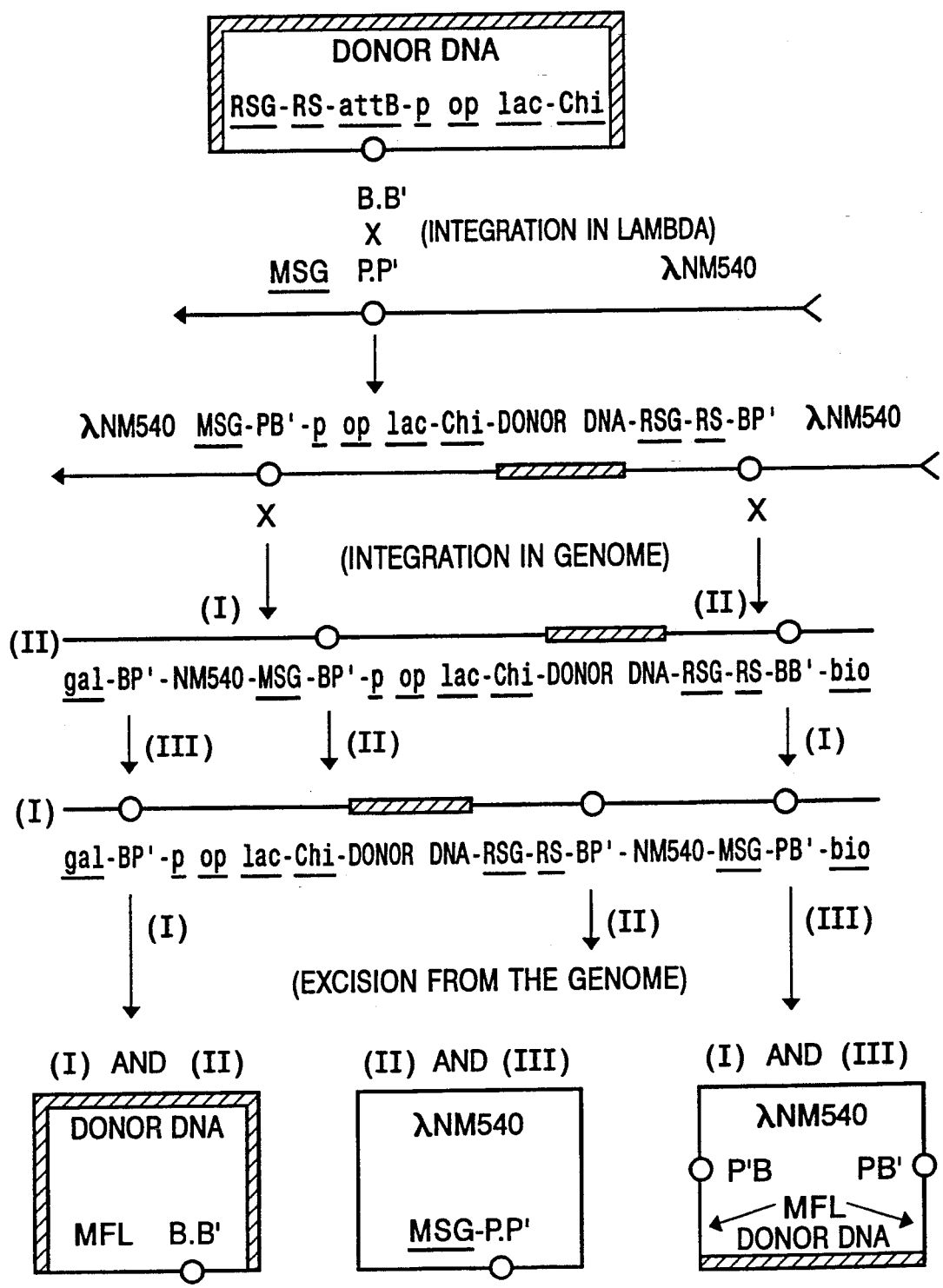

The designations used have the following meanings:
attB: integration site of phage lambda
Chi: crossing-over hot-spot instigator sequence
MSG: gene selectable in a microorganism
oriM: replication functions required in a microorganism
oriR: replication functions required in the receptor p op lac: promoter operator of the *E. coli* lac gene
RS: sequence homologous to a receptor sequence
RSG: gene selectable in the receptor.
The arrows indicate the orientation.

FIG. 2 diagrammatically shows the development in case of expression by integrative recombination.

In this figure gal is the galactose operon of *E. coli* and bio is the biotin operon of *E. Coli*.

DETAILED DESCRIPTION OF THE INVENTION

The first step of the process according to the invention comprises isolating the DNA of high molecular weight from the donor cell. This is then fragmented by means of an endonuclease (e.g., a restriction enzyme) in such a manner as to obtain fragments sufficiently large to contain one complete gene with its regulatory elements. The resulting fragments are now jointed to the multifunctional linker according to the invention by means of a ligase. The multifunctional linker is a linear DNA molecule which can have two different forms: a multifunctional linker capable of circularizing the donor DNA fragments or a multifunctional linker capable of providing these fragments at both ends with a hairpin structure. Consequently, ligation results in a DNA molecule containing the donor DNA and the multifunctional linker, either in the form of a linear structure, in the form of a circular structure or in the form of a linear structure with hairpin ends. The structures are shown in FIGS. 1C, 1D and 1E.

The multifunctional linker comprises at least one of the following elements:

(A) A DNA sequence homologous to a part of the receptor genome so as to enable (by crossing-over) recombination between the receptor genome and the inserted DNA which is composed of the multifunctional linker and donor DNA. As will be described with respect to the preparation of the multifunctional linker, this homologous part will usually be composed of at least 100 base pairs and originate from the receptor genome.

(B) An operator sequence enabling DNA containing the operator sequence to be recognized and separated, by means of interaction with the corresponding repressor protein. In principle, any operator sequence is suitable here, provided the repressor protein is sufficiently manageable. Suitable operator sequences are, e.g., the lac operator (lactose), the gal operator (galactose) and the trp operator (tryptophan), all of *E. coli*.

(C) A sequence enabling replication in a microorganism, preferably through integrative recombination in a vector, so that the multifunctional linker with the DNA coupled thereto can be multiplied in a host. Such a sequence is, e.g., the attB sequence enabling integration of the bacteriophage λ in *E. coli*. The sequence attB is: GCTTTTTTATACTAA.

(D) A sequence allowing expression of a gene in a microorganism to enable identification of transformants containing the multifunctional linker. This can be realized, e.g., (1) by incorporating a complete gene with an optionally controllable promoter. Expression can also be realized (2) by means of integrative recombination. Thus an optionally controllable promoter is cloned to the right of the attB sequence such that this promoter expresses a gene located to the left of the attP sequence on the λ vector (FIG. 2). It is clear that the elements (B), (C) and (D) in their simplest form may be restricted to the structure attB promoter/operator.

The process here described allows the donor DNA transmitted to the receptor to be selected and multiplied in a microorganism which has no recombination functions, e.g., *E. coli* recA to avoid that rearrangements or deletions occur in the donor DNA owing to these recombination functions. A suitable gene is the xylE gene of *Bacillus putida*, which—under control of the lac operator promoter during growth in the presence of isopropyl-$\beta$-D-thio-galactoside (IPTG) and catechol—gives rise to the formation of yellow colonies. Other suitable genes are, e.g., the bla gene ($\beta$-lactamase) causing resistance to penicillin, the aphII gene (kanamycin resistance) or the lacZ gene ($\beta$-galactosidase).

(E) A short DNA sequence containing at one end a suitable restriction sequence for joining to the multifunctional linker and at the other end a hairpin structure hiding a sequence which—only through replication of the unfolded hairpin structure—forms a substrate for a special restriction enzyme or endonuclease.

The purpose of attaching hairpin structures to the ends of the donor DNA is (1) to retain a linear structure facilitating the uptake through the pores of the membrane of the nucleus, (2) to protect the ends from exonucleases in the cell, and (3) to enable the recombination enzymes in the nucleus to convert the linear DNA into circular DNA. It is clear that to this end the linear donor DNA carries the multifunctional linker as a direct repetition at the ends, as shown in FIG. 1D. Donor DNA fragments containing the required elements, suitable for replication in the receptor (FIG. 1E), may be dimerized in the nucleus of the receptor cell. Thus, the restriction sites hidden in the top of the hairpin structure are released and can be recognized as such.

Preferably, the multifunctional linker additionally comprises a sequence stimulating the crossing-over, a so-called "crossing-over hot-spot instigator" or "chi" sequence, such as the chi sequence of *E. coli* K12: GCTGGTGG. (See Smith, G. R. et al., Cell 24, 429–436 (1981)).

Variants of chi sequences are also useful, although they sometimes have a lower activity (Cheng and Smith, J. Mol. Biol. 180, 371–377 (1984)). It is also possible here to use chi sequences of another origin, e.g., human origin (Jeffreys et al., Nature 314, 67–73 (1985)). Finally, it is also possible to incorporate a sequence which can occur in the form of Z DNA to promote integration.

It is further advantageous in the process according to the invention if the multifunctional linker also comprises a gene whose expression can be demonstrated in the receptor. Although the property to be transmitted to the receptor may sometimes be used itself in the step of screening or selecting the transformants, it is often desirable, especially when the property to be transmitted it not directly detectable, to include a property which is directly suitable for screening. In this connection antibiotic resistance genes are suitable when cells are to be transformed.

Preferably, the multifunctional linker according to the invention has the structure shown in FIG. 1A or 1B.

The next step of the process according to the invention for transforming cells is to transmit the donor DNA molecules joined with the multifunctional linker to the receptor cell, if required after a fractionation according to molecular weight. This transmission may take place by direct transformation methods, such as microinjection, electroporesis or natural uptake.

Subsequently, the receptor cells are screened, if desired, and those cells having taken up donor DNA coupled to the multifunctional linker are selected. Subsequently, DNA of high molecular weight is isolated from these receptor cells, which DNA is then fragmented with an endonuclease such that fragments are obtained sufficiently large to comprise one complete gene with the pertinent regulatory elements and the multifunctional linker. In order to prevent the linker from being cut loose from the transmitted DNA, it will be ensured beforehand that the joint with the multifunctional linker creates no new restriction sites for the endonuclease which was used for fragmenting the donor DNA.

Those fragments containing the operator sequence of the linker are now isolated from the mixture of DNA molecules. In this isolation the high affinity of the repressor protein to the corresponding operator sequence is utilized. DNA fragments binding repressor protein are isolated on filters by the method of Riggs et al., J. Mol. Biol. 53, 401 (1970).

After—or, if required, before—the isolation the DNA molecules are circularized by means of a ligase.

The resulting DNA molecules are each to be multiplied separately in order to have them available in sufficient amounts. To this end, microorganisms are transformed with the relevant DNA molecules. Fragments containing in the multifunctional linker the elements required for replication and selection can be multiplied as such in the microorganism. Fragments having in the multifunctional linker the sequence attB promoter operator can be multiplied and selected after transformation and in vivo integration in a suitable λ vector: e.g., λNM540 xylE. If the multifunctional linker contains, e.g., the attB sequence enabling integration in bacteriophage λ, the DNA sequences containing the multifunctional linker and isolated from the receptor can be integrated into the genome of a bacterial strain containing a lysogenic phage λ, such as *E. coli* MC 1061 (λNM450 XylE). After induction of the phage and plating out screening may be effected on plaques showing expression of the gene present on the multifunctional linker, the presence of which in microorganisms can be readily demonstrated. The presence of, e.g., the xylE gene can be easily recognized by the formation of yellow plaques when culturing is effected in the presence of IPTG and catechol is sprayed onto the plates. The positive plaques are isolated and purified one time by inoculating and isolating plaques. Culturing at low temperatures results in a series of lysogenic strains which are clones in λ of the multifunctional linker and donor sequences transmitted to the receptor. Thus a limited gene-bank of donor DNA transmitted to the receptor is available.

By transforming again a receptor with the DNA of a clone by means of direct transformation methods and screening it on transformants the donor DNA sequences transferred in the different clones can be correlated with the phenotypic expression in the receptor.

The process according to the invention therefore allows for transfer of genes from a donor to a receptor without requiring a previous extensive examination as to the correlation between specific genes and a phenotypic feature. Once suitable transformants have been obtained, these can be used directly. The financial profit thus made can be invested at a next stage in further research to more closely characterize the transformants, and more in particular the genes transmitted. It is of special advantage, then, that the first transformants still contain the multifunctional linker sequence, so that the transmitted DNA can be recognized in the receptor genome and can be isolated therefrom again by means of the interaction between the operator sequence located on the multifunctional linker and the pertinent repressor protein.

After the genes transmitted to the receptor have been obtained and characterized, a part of the multifunctional linker sequence may be removed from the receptor genome, if required. This may be desirable, because some elements of the linker are superfluous after the transformation and it is generally preferred to avoid superfluous changes in the receptor genome, especially since DNA foreign to the species will be concerned here in most cases. In this last case a short version of the multifunctional linker is used. The part of the multifunctional linker which is homologous to a part of the receptor genome, however, should normally remain present so as to be able to insert the DNA into the receptor genome again by means of recombination.

The process according to the invention has a wide range of application. Practice will teach where the limits of connection are within which the process can still be applied successfully. The transmission of genetic material will no doubt proceed more easily according as the connection between receptor and donor is stronger. Thus the process can be used successfully for transmitting specific features of a species to another variety of the same species or to another species of the same family or even to a species of another family.

As will appear from the experimental part, the process has already proved to be successful for the transformation of monocotyledonous plants with DNA from other monocotyledonous plants.

The multifunctional linker, which is an essential part of the invention, may be prepared in different ways, depending on the specific structure of the linker. In view of the size of the linker, which will generally be in the order of magnitude of about 3600 base pairs, it seems unattractive to prepare the total sequence synthetically. The progress in the synthesis of DNA sequences is so fast, however, that it may be possible before long to prepare such sequences fully synthetically by way of routine. Parts of the sequences, however, can be prepared synthetically anyway. In view of the large number of ways in which the multifunctional linker according to the invention and all its variants can be prepared, it is not possible to give a general prescription. In most cases, however, it will be clear to those skilled in the art of recombinant DNA how to prepare a specific multifunctional linker. The multifunctional linker and parts thereof may be produced and sold in the form of a kit. By way of illustration the preparation of the multifunctional linker according to the invention with the sequence shown in FIG. 1 will be described hereinbelow.

EXAMPLE I

Preparation of a Multifunctional Linker

A. according to FIG. 1A.

A multifunctional linker according to the invention is prepared having the structure shown in FIG. 1A. By way of example it is assumed that the linker will be used to transform DNA of a barley variety with the DNA of a wheat variety.

The linker has a length of about 3600 base pairs and contains the following elements:

1. The sequence attB of *Escherichia coli* K12: GCTTTTTTATACTAA

This sequence is sufficient for the integration of bacteriophage lambda (H. A. Nash, *Ann.Rev.Genetics* 15, 143-167, 1981).

The function of attB in the multifunctional linker is the integration of the linker, together with the genetic information covalently bound thereto, in bacteriophage lambda. The complete sequence is:

GCTGCAGCTTTTTTATACTAAGATCTGAATTC
PstI                             BglII     EcoRI

This sequence is chemically synthesized in a DNA synthesizer model Applied Biosystems 380 A.

The sequence PstI-attB-BglII-EcoRI is cloned in plasmid pBR322 cut with PstI and EcoRI and transformed to *E. coli* HB101. The integration of pBR322 in bacterio-phage lambda b506 cI857 (R. W. Davis & J. S. Parkinson 1971. *J.Mol.Biol.* 56, 403–423) is confirmed by the transfer of the tetracycline resistance in the strain *E. coli* C 600, made lysogenic by phage lamda. pBR322 (attB) is the source of the attB sequence with PstI and BglII ends.

The sequence PstI-attB-BglII is cloned in the pUC8 plasmid cut with BamHI and PstI. The structure of the clone and the attB function is confirmed by integration of the ampicillin resistance marker of pUC8 in phage λcI857 which is then capable of making *E. coli* JM109 lysogenic and ampicillin resistant at 30° C. Plasmid pUC8 (attB) is the source of the attB p op lac sequence with HaeII and PstI ends.

2. For further cloning plasmid Pi AN7 is called upon, the supF gene of which is replaced by the amp gene of pUC19. To achieve this, Pi AN7 is cut with XmnI and HaeII and pUC19 with AatII and HaeII, the fragments are blunt-ended with mung bean nuclease and isolated by means of agarose gel electrophoresis. The piAN7 fragment of 240 bp is ligated with the pUC19 fragment of 1560 bp to form Pi Amp 71 in which the EcoRI site of the MCS of Pi AN7 is restored and the HaeII site has disappeared. Of the two possible orientations the one restoring the replication sequence of Co1 E1 is retained. The cloning site (MCS) of Pi Amp 71 (MCS) is as follows:

(amp) EcoRI-XmaI-BamHI-AccI-PstI-BglII-XbaI-HindIII (ori). The crossing-over hot-spot instigator (Chi) of *E. coli* (G. R. Smith et al. 1981, Cell 24: 429-436) having the sequence: GCTGGTGG is chemically synthesized by means of an DNA synthesizer model Applied Biosystems 380A. The complete synthesized sequence is as follows: CTCTAGAGATCTGCTGGTGGCGCT-CTAGAGC (XbaI-BglII-Chi -HaeII-XbaI). This sequence cut with XbaI is cloned at the XbaI site of Pi Amp71. Of the two possible orientations the one losing the HaeII site after cutting with BglII and religating is retained. The resulting plasmid is further called Pi Amp 71 C and has the structure:

(amp)
EcoRI-XmaI-BamHI-AccI-PstI-BglII-XbaI-HaeII
-Chi-BglII-XbaI-HinIII(ori)

3. The PstI-attB-p op lac HaeII sequence is cloned therein after cutting with PstI and HaeII. Thus a plasmid Pi Amp71 ALC is obtained having the following structure:

(amp) EcoRI-XmaI--BamHI--AccI-PstI-attB-p op
lac-HaeII-Chi-BglII-XbaI-HinIII(ori)

4. Pi Amp71 ALC is generally useful for incorporating genes capable of being selected in the receptor and of a sequence derived from the receptor.

The example here chosen is useful in the transformation of barley with wheat DNA.

The chloramphenicol acetyl transferase gene with the regulatory elements of the nopaline synthase gene of *Agrobacterium tumefaciens* strain C58 (M. De Block et al. EMBO J 3 (1984) 1681-1689) is cloned as a ClaI fragment at the AccI site of Pi Amp71 ALC. Thus a plasmid Pi Amp71 CATALC is obtained having the structure:

(amp)
EcoRI-XmaI-BamHI-pnos-cat-3'nos-PstI-attB-p op
lac-HaeII-Chi-BglII-XbaI-HinIII(ori1 )

5. The DNA sequence which is homologous to a part of the barley receptor DNA is a so-called repeat sequence. Barley germ DNA is fragmented by means of ultrasound (sonication) into pieces having a length of approximately 1000 bp. After denaturation and renaturation the fragments having a Cot ½ value of 10E2 are isolated after treatment with S1 nuclease on hydroxyapatite as double strand DNA. These fragments are extended at the ends with oligo dC by means of terminal transferase and cloned at the PstI site of pUC19, the ends of which are extended with oligo dG by means of terminal transferase. From the cloned fragments one is selected having a length of approximately 1000 bp which hybridizes with approximately 1% of the other clones and contains no internal restriction sites for PstI, BamHI or BglII. This pUC19 plasmid further serves as a source for receptor repeat DNA with PstI ends. It should be noted that, if desired, it may be verified whether the cloned fragments occur in DNA which are expressed in a specific tissue (e.g., mesophyll) by using the footprinting technique. By this is meant the disappearance from chromatin of DNA sequences which are expressed, and this after treatment with DNAase.

The repeat sequence is now incorporated as a PstI fragment into the PstI site of Pi Amp71 CATALC. Two orientations are possible, and both are retained and used in transformation experiments. This final plasmid contains a complete multifunctional linker according to the invention with BamHI and BglII ends. This plasmid is designated further as Pi Amp71 CATRALC. After cutting from the vector this linker may be used to circularize donor DNA fragments with GATC ends, treated with phosphatase.

6. The hairpin structure used for the construction of linear donor DNA with multifunctional linkers at the ends has the following sequence:

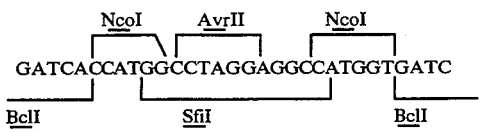

This sequence is chemically synthesized in a DNA synthesizer model Applied Biosystems 380A and cloned at the BamHI site of pUC19. The thus obtained pUCl 19H is the source of the hairpin sequence by cutting with Sau3A of the smallest PvuII fragment.

The hairpin structure is formed by denaturation and rapid renaturation of the thus obtained fragment and can be ligated both with the BamHI and the BglII ends of the multifunctional linker and with the GATC ends of the donor DNA. Two hairpin structures are formed which only differ in the bases at the top: AGG or CCT After replication, if any, of the unfolded hairpin structure an AvrII and a SfiI restriction sequence will be formed. The difference between the two structures resides in the exact localization of the AvrII site which is shifted by three nucleotides in one of both with respect to the other. The preparation of multifunctional linker with hairpin ends takes place as follows:
 1) to the right of the multifunctional linker. Pi Amp71 CATRALC is cut with BglII and ligated with the BclI end of the hairpin sequence. After transformation of the strain HB101 a circular dimer is formed by replication, which dimer gives the hairpin sequence between two MFLs after isolation and cutting with BamHI. Denaturation and rapid renaturation at a low concentration (1 μg/ml) results in the required structure with BamHI ends.
 2) to the left of the multifunctional linker. By cutting Pi Amp71 CATRALC with BamHI before ligating with the hairpin sequences and by cutting the dimer obtained in HB101 with BglII the hairpin structure to the left of the MFL is formed by a similar process.

Both multifunctional linkers with hairpin ends are now mixed in equal amounts and ligated with donor DNA fragments having GATC ends. It is clear that one specific fragment may occur in four different forms:

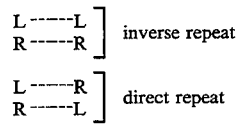

About 50% of the molecules obtained will bear the multifunctional linker as a direct repeat at the ends, the other molecules bear the linker as an inverse repeat.

The former can form, through recombination, circular molecules containing only one copy of the multifunctional linker. The latter can only form circular molecules if they contain the necessary elements enabling replication in the receptor.

B. According to FIG. 1B.

The vector for the construction of the multifunctional linker suitable for multiplication and selection in a microorganism is prepared as follows:
 1. The plasmid pUC19 is cut with AatII and blunt-ended with mung bean nuclease. Then it is cut again with EcoRI and the ends are blunt-ended with T4 DNA polymerase. By means of ligation of the large fragment (396-2617) a pUCl91 is obtained from which the lacZ gene has disappeared and the EcoRI site of the MCS has been restored.
 2. The XbaI-BglII-Chi-HaeII-XbaI sequence is cut with XbaI from Pi Amp71C and cloned in pUCl91, further designated as pUCl91COOL.
 3. The ClaI fragment with the chloramphenicol acetyl transferase gene with the regulatory elements of the nopaline synthase gene of Agrobacterium tumefaciens strain C58 is cloned at the AccI site of pUCl91COOL. Thus the plasmid pUCl91COOLCAT is obtained.
 4. The receptor repeat sequence is cut from vector pUC19 with PstI and cloned at the PstI site of pUCl9-1COOLCAT. This last plasmid is further designated as pUCl91COOLCATR and is in fact a circular form of the multifunctional linker according to FIG. 1B.
 5. The hairpin structures are attached in the same way as described for Pi Amp71 CATRALC.

EXAMPLE II

Transfer of Wheat Genes to Barley

A variety of wheat having a proper baking value (Triticum aestivum cultivar Rektor) is used as a donor. The DNA is isolated from chromatin of embryos produced by mills as a base material for wheat germ oil. The embryos are first defatted with chloroform 15% ethanol and then vacuum-dried. The embryos are then finely ground in liquid nitrogen and extracted at $-20°$ C. with Griesbach buffer (R. J. Griesbach et al. 1982 Plant Sci Lett 24: 55-60) to which glycerol is added up to a final concentration of 50%. The mixture is filtered through a nylon cloth (50 microns gauze) and then centrifuged off at 4000 g. The chromatin is separated from the starch layer, washed with Griesbach buffer several times and centrifuged twice through a pad of 2.3M saccharose in Griesbach buffer. The DNA is released from the resulting chromatin by addition of NaCl up to a concentration of 2M and deproteinized with a mixture of phenol, chloroform and isoamyl alcohol (50,48,2). The DNA is precipitated therefrom with ethanol dissolved in Tris 0.01M, EDTA 0.001M and once again precipitated with isopropanol in the presence of 0.3M sodium acetate. Then the DNA is dissolved in pure water. Parts of this DNA are cut with BamHI, BglII, XhoII, Sau3A, BclI or MboI or a mixture of these restriction enzymes, all of which give a 5' GATC end but have a different sensitivity to methylation of the restriction sequence and cut different restriction sites. The average size of the fragments is maintained at about 10,000 bp.

The resulting fragments are deprived of the end phosphate groups with phosphatase (calf's intestine phosphatase) and ligated with the multifunctional linker in such a manner that the donor DNA-linker joint contains at least no BamHI, BglII or BclI site (see table 1).

Circular molecules containing donor DNA and multifunctional linker are thus formed.

For the preparation of linear molecules with multifunctional linker and hairpin structures the donor DNA fragments are ligated with a mixture of left-hand and right-hand multifunctional linker molecules with hairpin ends.

The resulting donor DNA fragments coupled to multifunctional linker are separated from the linker on the basis of their molecular weight (2 Mdal against 8 to 10 Mdal). In accordance with the amount of DNA this may occur on an agarose gel by electrophoresis, by agarose screen chromatography or by gradient centrifugation. The circularized donor DNA and the linear donor DNA with hairpin ends can be purified by treatment with exonuclease.

The barley receptor plants are grown in pots in the greenhouse. About the moment when fertilization takes place the ears are opened, and with the aid of an Eppendorf micro-injector about 10 pL purified donor DNA coupled to multifunctional linker, circular or linear, is injected into the embryo sac, right through the wall of the ovary. The untreated ovaries are cut out, the chaffs are closed again and the treated ears are protected with a parchment pouch. The seeds of the thus obtained plants are tested for resistance to the antibiotic for which the resistance gene was inserted (e.g., chloramphenicol). The resistant germs are further grown in a greenhouse or in the open field in accordance with the season. Tests for the presence of the inserted donor DNA can now be conducted on young leaves of the resistant plants by using the functions located on the multifunctional linker, on the one hand, and by finding out which sequences are connected therewith. Total DNA is extracted according to the method of Lemmers et al. (1980) J. Mol. Biol. 144: (353-376) and decomposed with BamHI, BglII, BclI or Xho II depending on the employed restriction enzymes during construction of the inserted donor DNA (see table 1). By Southern hybridization with the sequence of the multifunctional linker it can be determined how many fragments of donor DNA have been retained in the barley genome. The size of the fragments is compared with a Southern hybridization between the donor DNA employed for the micro-injection and treated with the same restriction enzyme and the sequence of the multifunctional linker. Deviating sizes can indicate integration of the inserted donor DNA.

Of the seed of this first generation of treated barley plants (T1) a part of the endosperm is removed for SDS PAGE in order to find out which seeds show a different electrophoresis pattern of reverse proteins with respect to the original variety and which protein bands possibly correspond to those of the employed wheat variety (Rektor).

The obtaining of a barley variety with wheat proteins is a first result of the technique applied in this invention.

EXAMPLE III

This example describes a method to recover genes of a donor expressed in a receptor and screened or selected in the receptor on the basis thereof, by using the multifunctional linker. The method comprises the following steps:

1. Isolating DNA from the chromatin of the selected receptor.
2. Cutting this DNA with a restriction enzyme, in accordance with the examples in table 1.
3. Circularizing the thus obtained DNA fragments.
4. Separating DNA containing the multifunctional linker by using the lac operator repressor binding.
5. Transforming microorganisms with the circular DNA, with or without the use of a vector.
6. Screening or selecting microorganisms on the basis of expression of the gene located on the multifunctional linker.
7. Analyzing the thereby obtained limited gene-bank of donor DNA fragments transmitted to the receptor.
8. Reinserting individual donor DNA fragments into a receptor so as to correlate the fragments with the selected properties of the receptor.

The above described method can be applied in any generation of selected receptors. It is clear, however, that, in the case of sexual reproduction, the more generations distant from the treated generation, the less donor genes are found back in a specific individual. By selecting during different generations individuals can finally be obtained which have retained only those genes of the donor for which there is selected.

An application of the method to the T2 generation of barley plants from example II will be described hereinbelow.

Step 1

The seeds of the barley plants obtained on the T1 generation are tested for resistance to chloramphenicol (5 μg/ml), encoded by the plant-adapted cat gene in the multifunctional linker. Young leaves of the resistant plants are regularly harvested and stored in liquid nitrogen. The leaves of each plant are ground in a porcelain mortar with the aid of sand and a pestle, cooled with liquid nitrogen. Chromatin is isolated with the Griesbach buffer to which 50% glycerol has been added and is cooled to −20° C. The suspension is filtered through a 50 /um mesh nylon cloth. The chromatin is sedimented at 4000 g for 30 minutes, and the sediment is brought into suspension in Griesbach buffer. Cell decomposition products are removed by centrifugation at 100 g for 15 minutes. The supernatant is centrifuged over a pad of 2.3M saccharose in Griesbach buffer at 70,000 g for 2 hours. The sediment containing chromatin and starch grains is brought into suspension in 2M NaCl, pH 8, with the DNA being released.

The DNA solution is agitated with a mixture of phenol-chloroform-isoamyl alcohol (50/48/2) at pH 8. After separation of the phases the DNA is precipitated with cold (−20° C.) ethanol, dried with 96% ethanol and then with an air stream. The DNA is dissolved in Tris 0.01M, EDTA 0.001M, pH 8, and reprecipitated with isopropanol in the presence of 0.3M Na acetate. After drying again, the DNA is finally dissolved in pure water.

Step 2

Receptor DNA of plants transformed by BamHI cut donor DNA fragments is likewise cut with BamHI in this step under conditions indicated by the supplier with the understanding that BamHI ster activity is reduced to a minimum. The DNA cut is phenolized again, precipitated with ethanol and dissolved in pure water.

Step 3

A part of the DNA obtained is diluted to a concentration of 30 μg/ml and circularized by means of T4 DNA ligase under the conditions indicated by the supplier. The percentage of circular DNA is determined by electron microscopy.

Step 4

The DNA obtained in step 3 is isolated in the presence of lac repressor protein on a filter as described by Riggs et al. in J. Mol. Biol. 53: 401 (1970).

Step 5

If the donor DNA contained a multifunctional linker suitable for multiplication in a microorganism the filter is incubated at 30° C. with E. coli MC1061 recA bacteria, made competent according to the method by Dagert and Ehrlich (Gene 6: 23-29, 1979). If the donor DNA contained a multifunctional linker suitable for integration in a lambda vector use is made of MC1061 recA bacteria lysogenic to lambda NM540 A or X (N. Murray J. Mol. Biol. 98: 551 (1975, and see further)).

Phage lambda NM540 A is prepared as follows:

From plasmid pKC7 (Rao and Rogers Gene 7: 79–82 (1979)) the Aph3'II gene is cut with BglII and BamHI and cloned in PiAmp71 cut with BglII. After ligation it is cut again with EcoRI and HindIII and cloned in pUC8 cut with the same enzymes. Selected are kan$^R$ colonies in JM109. Lambda NM540 DNA has a unique HindIII site at position 27475 to the left of the attP sequence. The SalI Aph3'II HindIII fragment and a partial AvaI fragment of 1 to 19397 bp of phage lambda are ligated together therewith, and the phage is isolated after transfection. The thus obtained phage lambda NM540 A has all the functions required for integration of circular DNA with the AttB sequence and can account for its multiplication and infectivity in a recA strain. The NM540 A DNA has the following deletions: 7000 bp (from AvaI to SalI), 2300 bp (imm21 instead of immλ) and 2800 bp (nin5), a total of about 12,000 bp. This phage has only 75% of the lambda genome and can accommodate for up to 20,000 bp foreign DNA.

Lambda NM540 X is obtained in a similar manner. Then the SalI XylE HindIII fragment of RFI DNA of phage ml3 Tg 402 (Zukowski et al. Proc Nat Acad Sci USA 80: 1101–1105, 1983) is used.

The MC1061 recA bacteria lysogenic to lambda NM540 A or X are transformed at 30° C. for 20 minutes with the circular donor DNA coupled to multifunctional linker and then induced at 42° C. for 15 minutes. During the subsequent phage replication, because of the attB site on the multifunctional linker, the donor DNA is incorporated into the phage DNA by integrative recombination promoted by the integrase (int) of phage lambda. By this process the p op lac (promoter operator of the lacZgene) comes to rest before the XylE or the Aph3'II gene. The sequence contains a TAA stop codon in the reading frame of lacZ, followed by an ATG start codon of the XylE or Aph3'II gene (see FIG. 2).

By virtue of the presence of the λimm21 N gene product reading is continued by the RNA polymerase of E. coli.

Phages which have incorporated the donor DNA and the multifunctional linker into their DNA are recognized by their property of oxidizing in the presence of IPTG catechol in their host bacterium or imparting to the bacterium resistance to kanamycin, and this at 30° C.

The further procedure depends on the employed multifunctional linker and on whether the donor DNA is thus incorporated into a phage or can be treated as a plasmid.

A. The donor DNA is incorporated into lambda NM540 A or X. The phages are multiplied at 42° C. and the lysate is subjected to a cesium formate gradient centrifugation. The fractions of the gradient containing phages having a lower density than the parental phage and therefore containing more DNA are used to lysogenize MC1061 recA bacteria at 30° C. There is thus obtained a limited DNA bank of donor DNA fragments which have already been separated into some thirty fractions according to their molecular weight. The percentage of xylE+ or kanR colonies is determined and a part is stored in liquid nitrogen after addition of 20% glycerol.

As is apparent from the diagram of FIG. 2, only those lysogenic bacteria which have incorporated the lambda vector through int recombination at the BP' site are still capable of giving xylE+ or kanR colonies. In those bacteria in which the lambda vector is integrated into the PB' site the lac promoter operator is separated from the xylE or kanR gene.

For practical reasons the procedure is continued only with the first mentioned lysogenic bacteria.

Induction of these lysogenic bacteria results in that after 20 minutes three circular DNA molecules have been obtained in the bacteria: the NM540A or X DNA; the donor DNA joined to multifunctional linker; and the cointegrate of both. These molecules can be separated by agarose gel electrophoresis or by saccharose gradient centrifugation by virtue of their magnitude: respectively 36500 bp, 14000±6000 bp and 50500±6000 bp. (See FIG. 2).

B. By virtue of the multifunctional linker the donor DNA can be multiplied and selected as a plasmid in E. coli. Individual ampR colonies are tested for the size of the donor DNA by the method of Birnboim and Doly (Nuc Ac Res 7: 1513–1523 (1979)). If multifunctional linker and hairpin ends were used in the preparation of the donor DNA, there is cut with the restriction enzymes for those sites in the hairpin structure which are only formed by replication of the donor DNA, before its integration into the genome of the receptor: AvrII and SfiI. By cutting the resulting donor DNA as a plasmid with, e.g., XbaI and AvrII and by XbaI and SfiI, it can be examined whether the same fragments are formed. The finding of donor DNA fragments having a sequence suitable for replication in the receptor is a clear application of the invention here described.

The use of this sequence in the multifunctional linker instead of the sequence of the receptor as a homology range for integration is a further step in the development of this invention.

The two presently described methods of isolation of donor DNA fragments transmitted to the receptor both have advantages and drawbacks; the use of both methods allows an optimum characterization of the donor DNA constructions with multifunctional linker and hairpin ends after their passage in the receptor.

Both the circular DNA molecules isolated after phage induction as described under A and the plasmids isolated under B are used individually or in combinations for direct transformation of new receptor barley plants so as to provide the correlation with, e.g., reserve proteins of the wheat donor DNA.

EXAMPLE IV

Transmission of resistance to *Scizaphis* (*Toxoptera*) *granium* from a resistant barley variety to a sensitive wheat variety.

The donor used is a Toxoptera resistant variety of barley. It is known that the resistant varieties produce more benzyl alcohol (P. S. Juneja et al., 1972 Ann Entomol Soc Am65, 961–964). Chromatin is isolated from the germs of a resistant barley line. To this end, the barley grains are first ground for a short time, and the germs are screened with a 1 mm mesh screen. The germs are homogenized with sand in a mortar-with-pestle at the temperature of liquid nitrogen. The homogenisate is incorporated into Griesbach buffer to which glycerol is added up to a final concentration of 50% at −20° C. (R. J. Griesbach et al.; 1982, Plant Sci. Lett. 24: 55–60). The resulting suspension is filtered successively through three layers of gauze, a layer of Miracloth and a nylon cloth having 60/um pores. The filtrate is centrifuged off at 10,000 g for 15 minutes, and the sediment is washed three times with 0.15M NaCl pH 7. The chromatin is then centrifuged through a pad of 2.3M saccharose, always in the presence of 0.15M NaCl pH 7. Chromatin and starch grains are then extracted at 2M NaCl with a mixture of phenol/chloroform/isoamyl alcohol (50/48/2). The starch and the organic phase are centrifuged off, and the DNA is precipitated with ice-cold ethanol. After dissolving the precipitate in Tris 0.01M, EDTA 0.001M pH 8, the DNA is precipitated again with isopropanol after addition of Na acetate to 0.3M, and the precipitate is dissolved in pure water. A part of the DNA is digested with BamHI, another part with BglII and yet another part with XhoII. These restriction enzymes are insensitive to methylation of the DNA and give fragments having an average length of 5000 bp. A part of the fragments is ligated with the multifunctional linker in a concentration of approximately 10 μg/ml for the preparation of circular molecules, and a part is ligated with multifunctional linker with hairpin ends in a concentration of approximately 2 μg/ml for the preparation of linear molecules. Both preparations are purified from respectively noncircular DNA and linear DNA without hairpin ends by treatment with exonuclease V. After phenolization, precipitation and redissolving in pure water the donor DNA is ready for injection.

The wheat receptor plants are grown in the greenhouse. About the moment when the fertilization takes place the ears are opened, and with the aid of an Eppendorf micro-injector approximately 20 pl DNA solution having a concentration of approximately 500 μg/ml is injected into the embryo sac, right through the wall of the ovary. After the injection the chaffs are closed again, and the treated ears are shielded with a parchment pouch.

The half-ripe seed is harvested and exposed a few times to cold and heat for a couple of days (4° C. and 45° C.) in order to break the seed dormancy. Subsequently, the seeds are tested for germination in the presence of 25 μg/ml chloramphenicol, for which the resistance gene is located on the multifunctional linker. The resistant seeds are further grown in a greenhouse or in the open field, depending on the season.

During ripening of the grains on these plants the leaves are occupied with *Toxoptera granium*. The population is observed daily, and the plants which no longer accommodate insects are occupied with them again. Plants accommodating few, if any, insects after four weeks are considered resistant. The seed of the resistant plants is sown on ear lines, and the plants are carefully observed for morphological features departing from those of the original variety. The content of benzyl alcohol is determined as described by P. S. Juneja et al., 1975, Plant Physiol 56: 385-389.

The DNA fragment giving rise to an increased production of benzyl alcohol may then be identified in the same manner as discussed in Example III.

TABLE 1

| donor DNA | linker | joint can be cut by | | | | |
|---|---|---|---|---|---|---|
| cut with | end | BamHI | BglII | BclI | XhoII | Sau3A |
| BamHI | BglII | – | – | – | – | + |
| BglII | BamHI | – | – | – | + | + |
| BclI | BglII | – | – | – | – | + |
| BclI | BamHI | – | – | – | – | + |
| XhoII | BglII | – | +/– | – | + | + |
| XhoII | BamHI | +/– | – | – | + | + |

TABLE 1-continued

Bacteria, phages and plasmids

| | |
|---|---|
| Bacteria | |
| MC 1061 | Casadaban MJ Cohen SN J. Mol. Biol. 138, 179-207, 1980 |
| C600 | Appleyard R. Genetics 39, 429, 1954 |
| MB101 | Boyer, H. W., Rolland Dussoix D. J. Mol. Biol. 41, 459-472, 1969 |
| JM109 | Yanisch-Perron, C., Vieira, J., Messing, J. Gene 33, 103-119, 1985 |
| Phages | |
| λNM540 | Cloning Vectors P. M. Pauwels, Elsevier 1985 |
| λb506 | CI, 857 Davis & Parkinson, 1971 |
| λCI, 857 | Sussman, R., Jacob, F., Compt. Rend. Acad. Sci Paris 254, 1417, 1962 |
| Plasmids | |
| pBR322 | |
| pUC8 | Cloning Vectors P. M. Pauwels, Elsevier 1985 |
| pUC9 | |
| pUC19 | |
| PiAN7 | Catalogue New England Biolabs 1986/1987 |

I claim:

1. A multifunctional linker for transforming a receptor cell which is a linear DNA molecule comprising:
a. a DNA sequence comprising at least 100 base pairs;
b. an *E. coli* operator DNA sequence, which is the lac operator, the gal operator or the trp operator;
c. a sequence effective for replication in a microorganism or for integrative recombination in a vector, which latter is the attB sequence effective for integration in bacteriophage λ;
d. a regulatory sequence effective for expression of a gene in a microorganism;
a DNA sequence containing at one end a suitable restriction sequence for joining to the multifunctional linker and at the other end a hairpin structure hiding a sequence which forms a substrate for a restriction endonuclease;
f. a DNA sequence which promotes recombination which is a Z DNA sequence or a crossing-over hot spot instigator (chi) sequence; and
g. a sequence of a promotor whose expression can be demonstrated in a microorganism, after recombination of the inserted DNA comprising the multifunctional linker and donor DNA into a suitable bacteriophage λ vector.

2. The multifunctional linker according to claim 1 wherein, in the sequence effective for expression of a gene in a microorganism, the gene includes a promotor.

3. The multifunctional linker according to claim 1 wherein in the promotor sequence effective for expression of a gene in a microorganism, expression is realized by means of integrative recombination.

4. The multifunctional linker according to claim 1 wherein the *E. coli* operator DNA sequence, the sequence effective for replication in a microorganism or for integrative recombination in a vector and the sequence effective for expression of a gene in a microorganism are consisting of the structure attB promotor-/operator.

5. The multifunctional linker according to claim 1 wherein, in the sequence effective for expression of a gene in a microorganism, the gene is the xylE gene of Bacillus putida, the bla gene, the aphII gene or the lacZ gene.

6. The multifunctional linker according to claim 1 wherein the DNA sequence which promotes recombination is the chi sequence of *E. coli* K12.

7. The multifunctional linker according to claim 1 wherein the sequence of a promoter whose expression can be demonstrated in a microorganism is a sequence of an antibiotic resistance gene.

8. The multifunctional liner according to claim 1 wherein the microorganism is a Gram negative bacterium.

9. The multifunctional linker according to claim 1 wherein the microorganism is *E. coli.*

10. A process for transforming a receptor cell which comprises:
   a. isolating high molecular weight DNA from donor cells;
   b. degrading the donor cell DNA by means of an endonuclease into fragments comprising at least one gene and its regulatory elements;
   c. attaching to the ends of the resulting donor cell DNA fragments the multifunctional linker of claim 1 to which terminal hairpin structures have optionally been attached;
   d. transmitting the donor cell DNA fragments coupled to the multifunctional linker by means of direct transformation methods to the receptor cell; and
   e. screening the receptor cells expressing the donor DNA.

11. The process of claim 10 further comprising:
   a. isolating high molecular weight DNA form all of the receptor cells or from selected receptor cells;
   b. degrading the receptor cell DNA by means of endonuclease into fragments comprising one gene with its regulatory elements and a multifunctinal linker for transforming a receptor cell which is a linear DNA molecule comprising:
      i. a DNA sequence comprising at least 100 base pairs;
      ii. an *E. coli* operator DNA sequence, which is the lac operator, the gal operator or the trp operator;
      iii. a sequence effective for replication in a microorganism or for integrative recombination in a vector, which latter is the attB sequence effective for integration in bacteriophage λ;
      iv. a regulatory sequence effective for expression of a gene in a microorganism;
      v. a DNA sequence containing at one end a suitable restriction sequence for joining to the multifunctional linker and at the other end a hairpin structure hiding a sequence which forms a substrate for a restriction endonuclease;
      vi. a DNA sequence which promotes recombination which is a Z DNA sequence or a crossing-over hot spot instigator (chi) sequence; and
      vii. a sequence of a promoter whose expression can be demonstrated in a microorganism, after recombination of the inserted DNA comprising the multifunctional linker and donor DNA into a suitable bacteriophage λ vector;
   c. isolating form the mixture of resulting DNA fragments those fragments containing an *E. coli* operator DNA sequence which is the lac operator, the gal operator or the trp operator by using the binding force of the corresponding repressor protein;
   d. circularizing the isolated DNA fragments or inserting the isolated fragments into a vector;
   e. multiplying the circularized fragments or the vectors containing the fragments in a microorganism to obtain a limited gene ban of the sequences transmitted to the receptor cell; and
   f. transmitting the different sequences again through direct transformation to a receptor and selecting transformants expressing the donor DNA.

12. A process for transforming a receptor cell which comprises:
   a. isolating high molecular weight DNA from donor cells;
   b. degrading the donor cell DNA by means of an endonuclease into fragments comprising at least one gene and its regulatory elements;
   c. attaching to the ends of the resulting donor cell DNA fragments the multifunctional linker of claim 1;
   d. circularizing the resulting donor cell DNA fragments coupled to the multifunctional linker;
   e. transmitting the donor cell DNA fragments coupled to the multifunctional linker by means of direct transformation methods to the receptor cell; and
   f. screening the receptor cells expressing the donor DNA.

13. The process of claim 12 further comprising:
   a. isolating high molecular weight DNA from all of the receptor cells or from selected receptor cells;
   b. degrading the receptor cell DNA by means of endonuclease into fragments comprising one gene with its regulatory elements and a multifunctional linker comprising
      i. a DNA sequence comprising at least 100 base pairs;
      ii. an *E. coli* operator DNA sequence, which is the lac operator, the gel operator or the trp operator;
      iii. a sequence effective for replication in a microorganism or for integrative recombination in a vector, which latter is the attB sequence effective for integration in bacteriophage λ;
      iv. a regulatory sequence effective for expression of a gene in a microorganism;
      v. a DNA sequence containing at one end a suitable restriction sequence for joining to the multifunctional linker and at the other end a hairpin structure hiding a sequence which forms a substrate for a restriction endonuclease;
      vi. a DNA sequence which promotes recombination which is a Z DNA sequence or a crossing-over hot spot instigator (chi) sequence; and
      vii. a sequence of a promoter whose expression can be demonstrated in a microorganism, after recombination of the inserted DNA comprising the multifunctional linker and donor DNA into a suitable bactieriophage λ vector;
   c. isolating form the mixture of resulting DNA fragments those fragments containing an *E. coli* operator DNA sequence which is the lac operator, the gal operator or the trp operator by using the binding force of the corresponding repressor protein;
   d. circularizing the isolated DNA fragments or inserting the isolated fragments into a vector;
   e. multiplying the circularized fragments or the vectors containing the fragments in a microorganism to obtain a limited gene bank of the sequences transmitted to the receptor cell; and
   f. transmitting the different sequences again through direct transformation to a receptor and selecting transformants: expressing the donor DNA.

* * * * *